United States Patent [19]

Leone

[11] Patent Number: 5,318,531
[45] Date of Patent: Jun. 7, 1994

[54] INFUSION BALLOON CATHETER

[75] Inventor: James E. Leone, Miami, Fla.

[73] Assignee: Cordis Corporation, Miami Lakes, Fla.

[21] Appl. No.: 912,318

[22] Filed: Jul. 13, 1992

Related U.S. Application Data

[63] Continuation-in-part of Ser. No. 714,003, Jun. 11, 1991, Pat. No. 5,213,576.

[51] Int. Cl.⁵ .................. A61M 29/00; A61K 9/22
[52] U.S. Cl. .................. 604/96; 604/101; 604/892.1
[58] Field of Search .......... 604/890.1–892.1, 604/96–103, 53.54; 606/192–196; 128/202.15; 600/18

[56] References Cited

U.S. PATENT DOCUMENTS

| | | |
|---|---|---|
| 3,173,418 | 3/1965 | Baran . |
| 3,981,299 | 9/1976 | Murray . |
| 4,417,576 | 11/1983 | Baran . |
| 4,423,725 | 1/1984 | Baran et al. . |
| 4,821,722 | 4/1989 | Miller et al. . |
| 4,994,033 | 2/1991 | Shockey et al. . |
| 5,021,044 | 6/1991 | Sharkawy .................. 604/53 |
| 5,049,132 | 9/1991 | Shaffer et al. . |
| 5,087,244 | 2/1992 | Wolinsky et al. . |
| 5,098,381 | 3/1992 | Schneider . |
| 5,176,638 | 1/1993 | Michael .................. 604/101 |
| 5,199,951 | 4/1993 | Spears .................. 604/96 |

FOREIGN PATENT DOCUMENTS

| | | | |
|---|---|---|---|
| 8017099 | 8/1989 | Australia | 606/194 |
| 0383429 | 8/1990 | European Pat. Off. . | |
| WO89/12478 | 12/1989 | PCT Int'l Appl. . | |

OTHER PUBLICATIONS

Poretics Corporation 1990 Microfiltration Products Catalog, pp. 1–14, 27, Mar. 1, 1989.

Primary Examiner—John D. Yasko
Assistant Examiner—Adam J. Cermak
Attorney, Agent, or Firm—Gerstman & Ellis, Ltd.

[57] ABSTRACT

A balloon catheter comprises a catheter shaft and a balloon carried on the shaft, an inflation lumen being provided. The balloon comprises a plurality of holes of a size to permit medication delivered through the lumen to pass outwardly through the holes. The balloon carries on an outer surface a substantially hydrophilic, tubular microporous membrane covering the holes, to break up streams of flowing medication.

15 Claims, 1 Drawing Sheet

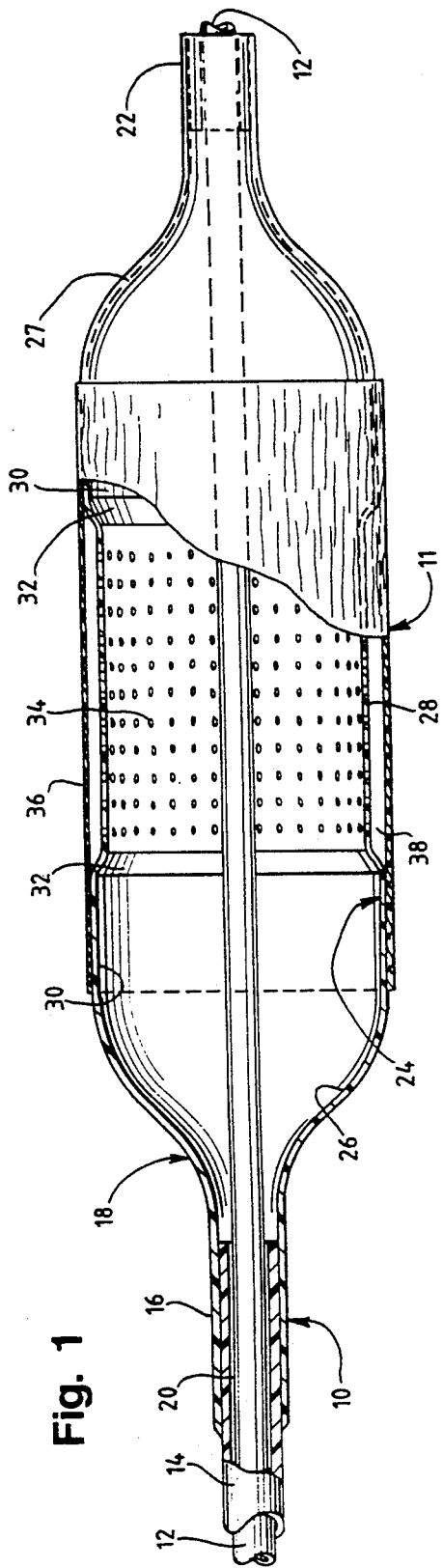
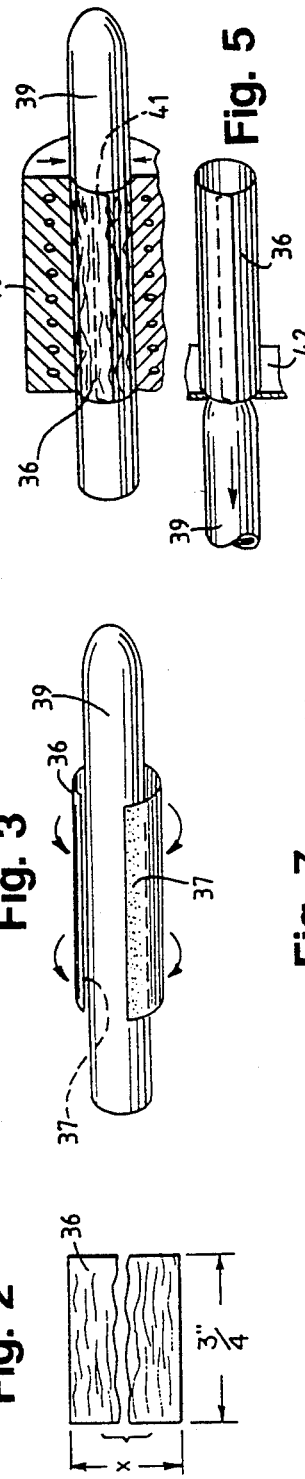
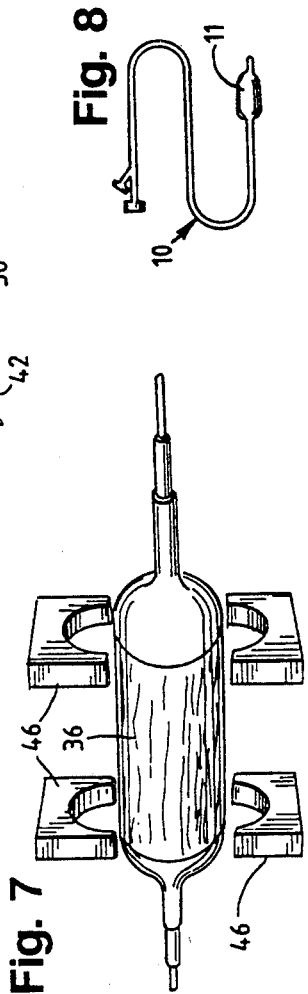
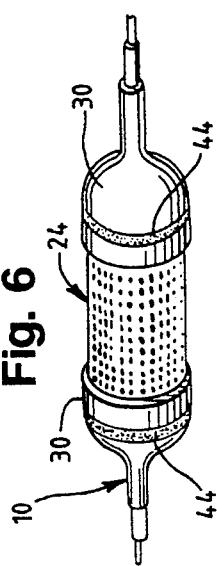
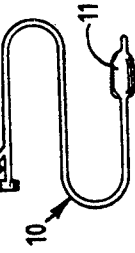

INFUSION BALLOON CATHETER

CROSS REFERENCE TO RELATED APPLICATION

This is a continuation-in-part of U.S. application Ser. No. 07/714,003, filed Jun. 11, 1991; now U.S. Pat. No. 5,213,576.

BACKGROUND OF THE INVENTION

In the prior art, for example Shockey et al. U.S. Pat. No. 4,994,033 and the C. R. Bard Inc. European Patent Application No. 383,429A2, published Aug. 22, 1990, a catheter is taught for the application of medication to a blood vessel wall, for example to a stenosis. The medication is administered through a balloon in the catheter which carries an array of minute holes or micropores, so that the medication may flow into the balloon through a lumen in the catheter, and then by the action of pressurization in the balloon it is forced out of the holes or micropores.

It has been found that at pressures of about two atmospheres and above, the velocity of fluid that passes out of the holes of such a balloon often can create a forceful stream which directly impinges the arterial wall. This, in turn, can actually cause tissue damage, even to the extent of extending and increasing a dissection within the arterial wall which is caused by an angioplasty procedure such as PCTA.

Thus there is a need for an infusion balloon catheter for administering medication to the arterial wall in which the medication can be administered under a reasonable pressure for rapid flow of medication out of a single perforated balloon, but the forceful streams are avoided, so that the fluid does not forcefully impinge against the arterial wall, but rather it diffuses out of the perforations in a substantial but non-damaging manner.

Baran U.S. Pat. No. 4,417,576 discloses a double-wall surgical cuff in which a surgical fluid such as an anesthetic may be inserted in a sponge rubber material emplaced between the two surgical cuffs. The outer surgical cuff is perforated, so that the surgical fluid can pass out outwardly through the outer surgical cuff, while the inner surgical cuff is not perforated. This relatively complex device may have a substantially increased outer diameter due to the presence of the two balloons and the sponge rubber, which restricts its entry into the smallest of arteries and the like.

DESCRIPTION OF THE INVENTION

In accordance with this invention a balloon catheter comprises a catheter shaft and a typically single balloon carried on the catheter shaft. A lumen is defined by the catheter shaft which communicates between a space located within the balloon and a proximal end portion of the catheter shaft. The balloon comprises a plurality of holes of a size to permit medication delivered through the lumen to pass outwardly through the holes. The balloon also has an outer surface, which outer surface carries a tubular, substantially hydrophilic, microporous membrane covering the holes of the balloon, to break up streams of flowing medication.

Preferably, the substantially hydrophilic, microporous membrane is the outermost member of the balloon catheter, surrounding the single balloon, typically without any inner balloon. However, if desired, an inner balloon may be provided, being of the standard inflatable balloon type to inflate the outer balloon and microporous membrane into firm contact with tissues as the medication is administered.

Preferably the balloon defines a generally cylindrical portion, plus tapered end portions having minimum diameter ends adhered to the catheter shaft. The tubular, microporous membrane is preferably carried by the cylindrical portion of the balloon and spaced from the tapered end portions.

A central portion of the generally cylindrical balloon portion may be of less diameter than the ends of the balloon cylindrical portion, typically with the central portion and the end portions being respectively separated by an annular step portion. Thus, a generally cylindrical space may be normally defined between central portions of the balloon and the microporous membrane in those circumstances where the microporous membrane ends are sealed to the ends of the balloon cylindrical portion.

It is generally preferred for the micropores of the membrane to be smaller and more numerous than the holes of the balloon. For example, the micropores of the membrane may be essentially from 0.4 to 3 microns in diameter, while the holes of the balloon are typically from 5 to 100 microns in diameter. Also, the typical number of the micropores per square centimeter of membrane may be from about one hundred thousand to five hundred million, while the number of the holes in the balloon may be essentially from twenty to one thousand. Also, the microporous membrane may be coated with a hydrophilic agent such as polyvinylpyrrolidone to improve the penetrability of medications through the micropores of the microporous membrane.

The microporous membrane may, for example, be a polycarbonate membrane manufactured by The Poretics Company specifically their TRACK-ETCH PCTE membrane filters, which are manufactured by exposing thin polycarbonate film to collimated, charged particles in a nuclear reactor. Then, the tracks left by the particles are preferentially etched to form uniform, cylindrical pores of predetermined pore size.

Specifically, one suitable hydrophilic, microporous membrane is a TRACK-ETCH PCTE membrane having a pore size of about 0.8 micron and a pore density of about thirty million pores per square centimeter. Such a membrane weighs about 1 milligram per square centimeter, having a thickness of about 9 microns and a water bubble point of about 18 p.s.i. Typically flow rates of water through such a membrane are about 215 ml. per minute per $cm^2$, using prefiltered water at 10 p.s.i. The above data comes from the manufacturer of the polycarbonate screen membrane.

The catheter of this invention may be a standard catheter for intravenous usage such as a PTCA dilatation catheter of low profile, in which the balloon has been perforated with holes having a diameter of approximately 20 to 30 microns (nominally 25 microns). In one embodiment, 64 of such 25 micron holes are present in a balloon which is about 20 millimeters in length and having a diameter of, typically, 2 to 4 millimeters (inflated). Such a balloon may be carried upon an otherwise conventional PTCA catheter having a useable length of 135 cm., and a catheter shaft diameter of 4.0 French or smaller. A guidewire may be used having a diameter of 0.018 millimeter, and the tip length of the catheter may be about 0.2 inch. The balloon may be made of 75 Shore D nylon.

DESCRIPTION OF DRAWINGS

FIG. 1 is a fragmentary, elevational view taken partly in section of an otherwise-conventional PTCA catheter, showing the modified balloon and overlying tubular, substantially hydrophilic, microporous membrane;

FIG. 2 is a plan view with a portion broken away of the membrane, while FIGS. 3 through 7 are perspective views showing steps in the manufacture and assembly of the catheter portion illustrated in FIG. 1; and FIG. 8 is a plan view of the catheter of FIG. 1.

DESCRIPTION OF SPECIFIC EMBODIMENTS

Referring to FIG. 1, the balloon section 11 of a PTCA dilatation catheter 10 of low profile is shown, similar in design to the HELIX catheter sold by the Cordis Corporation of Miami, Fla., except for the differences described herein.

Catheter 10 comprises an inner catheter body 12 which typically extends the entire length of the catheter, surrounded by an outer catheter body 14, which extends the length of the catheter up to its engagement by sealing with proximal end 16 of balloon 18.

Inner and outer catheter bodies 12, 14 together define a tubular space or inflation lumen 20 which may be used to provide liquid medication or inflation fluid to the interior of tubular balloon 18. Proximal balloon end 16, is sealed in conventional manner to a proximal portion of outer catheter body 14. Balloon 18 is sealed at its distal end 22 to inner catheter body 12.

Balloon 18 is made of nylon, PET, or another flexible but relatively inelastic material, defining, in its as-molded configuration, a generally cylindrical portion 24 and tapered end portions 26, 27 which taper down to their minimum diameter ends 16, 22. At ends 16, 22 balloon 18 is adhered to the respective portions of the catheter shaft, namely inner and outer catheter bodies 12, 14 as described above.

The generally cylindrical balloon portion 24, in turn, is shown to define a central portion 28 that is of less diameter than the end portions 30 of the balloon cylindrical portion 24, being separated from each other by annular step portions 32. Central portion 28 carries an array of holes 34 which, as described above, may have a diameter on the order of 25 microns each. Thus, medication passing through lumen 20 into the interior of balloon 18 can flow out of the holes 34 defined in central portion 28 of the balloon.

Tubular, hydrophilic microporous membrane 36 is carried on the generally cylindrical portion 24 of the balloon, with the respective ends of tubular, hydrophilic, microporous membrane 36 being adhered by gluing or heat sealing to the ends 30 of the balloon cylindrical portion 24. As a result of this, a generally cylindrical space 38 is normally defined between central portion 28 and microporous membrane 36.

The advantage of this is to provide in cylindrical space 38 a manifold which permits medication to migrate from holes 34 through the manifold into intimate contact with a relatively large area of microporous membrane 36. Thus, even though the micropores of membrane 36 may be much smaller than the holes 34 of the balloon, a good flow of medication through microporous membrane 36 is assured because of the exposure of the medication to vast numbers of the micropores. In the absence of a reduced diameter central section 28, where the cylindrical portion of the balloon is all of one diameter, much of the area of microporous, tubular membrane 36, spaced from the holes 34 of balloon 26, would be blocked by engagement with flat, port-free balloon material, and thus would not be available for participating in the transport of medication through microporous membrane 36. The result of this would be a much lower flow capacity of medicament through microporous membrane 36.

Thus, a balloon catheter is provided in which the outer diameter of the balloon in its deflated configuration is scarcely larger than the similar outer diameter of conventional and effective arterial catheters which are capable of penetration into small, branched coronary arteries and the like. Nevertheless, the catheter of this invention is capable of administering to a patient a medication such as an anticoagulant, an agent for preventing late restenosis, such as heparin, streptokinase, tissue plasminogen activator, prostaglandin E, or any other desired therapeutic agent. Another therapeutic agent may comprise vasodilatators to counteract vasospasm such as papaverine, or biological adhesives such as medical grade cyanoacrylate adhesive or fibrin glue, for purposes of gluing an occluding flap of tissue in a coronary artery to the wall, or the like. The catheter of this invention provides a good-supply of such medication, but without a forceful stream that can cause tissue damage. Rather, the medication can diffuse through the outer, tubular microporous membrane, but in a relatively abundant supply over a relatively substantial area of the microporous membrane.

While microporous membrane 36 may comprise a single ply of plastic having holes in it, it also may be a somewhat thicker fibrous web of plastic material having typically a myriad of micropores, to perform in a manner similar to that disclosed in the specific embodiment of this invention.

Referring to FIGS. 3 through 7, the process of manufacturing the balloon assembly shown in FIG. 1 is disclosed.

FIG. 2 shows a rectangular sheet of the polycarbonate, microporous membrane 36, prior to forming into a tubular configuration. Typically the length of membrane 36 may be ¾ inch, while the width X may be that dimension which is necessary to provide a cylinder of desired diameter as shown in FIG. 3.

In FIG. 3, the sheet of membrane 36 is wrapped in cylindrical, overlapping manner at 41 for sealing with a plastic adhesive diluted three fold with methylethyleketone, and wrapped in overlapping relationship of the opposed edges 37 about a metal mandrel 39, to assist in forming of a glued cylinder of said microporous membrane of the desired diameter.

Then, microporous membrane tube 36 may be heated to about 250° F. in a heater 40 while carried on mandrel 39. After this, as shown in FIG. 5, microporous membrane cylinder 36 is removed from mandrel 39. A sliding gripper 42 of any desired kind may be used for such removal.

Then, as shown in FIG. 6, the balloon portion 24 of catheter 10 may be coated with a series of generally annular seal lines 44 about the two end portions 30 of the balloon generally cylindrical portion. A conventional plastic adhesive may be used to form such seal line.

As shown in FIG. 7, cylinder 36 of microporous membrane is placed over the balloon cylindrical section 24, and annular heating dies 46 may be applied to overlie the adhesive lines 44 where they join with cylindrical membrane 36. Then, the application of heat and firm pressure for about 10 minutes at about 250° F. can cause permanent attachment of cylindrical membrane 36 in a sealing manner, so that the ends of cylindrical space 38 are well sealed, to manufacture the balloon of this invention on a conventional catheter.

The above has been offered for illustrative purposes only, and is not intended to limit the scope of the invention of this application, which is as defined in the claims below.

That which is claimed is:

1. A balloon catheter which comprises a catheter shaft and a balloon carried on said catheter shaft, a lumen defined by said catheter shaft which communicates between a space located within said balloon and a proximal end portion of said catheter shaft, said balloon comprising a plurality of holes of a size to permit medication delivered through said lumen to pass outwardly through said holes, said balloon having an outer surface and carrying on said outer surface a tubular, substantially hydrophilic, microporous membrane covering said holes to break up streams of flowing medication.

2. The catheter of claim 1 in which said balloon defines a central, generally cylindrical portion and tapered end portions having minimum diameter ends adhered to the catheter shaft, said tubular, microporous membrane being carried by the cylindrical portion of said balloon and spaced from the tapered end portions.

3. The catheter of claim 2 in which said balloon defines a central portion of said generally cylindrical portion that is of less diameter than ends of said cylindrical portion, whereby a generally cylindrical space is normally defined between central portions of said balloon and said microporous membrane.

4. The catheter of claim 1 in which said tubular, microporous, membrane is made of polycarbonate resin.

5. The catheter of claim 1 in which the micropores of said membrane are smaller and more numerous than the holes of said balloon.

6. The catheter of claim 1 in which the micropores of said membrane are essentially from 0.4 to 3 microns in diameter, the holes of said balloon being essentially from 5 to 100 microns in diameter.

7. The catheter of claim 1 in which the number of said micropores per square centimeter of said membrane is about one hundred thousand to five hundred million.

8. The catheter of claim 7 in which the number of said holes in the balloon is essentially from 20 to 1000.

9. The catheter of claim 1 in which said microporous membrane is coated with a hydrophilic agent.

10. A balloon catheter which comprises a catheter shaft and a balloon carried on said catheter shaft, a lumen defined by said catheter shaft which communicates between a space located within said balloon and a proximal end portion of said catheter shaft, said balloon comprising a plurality of holes of a size to permit medication delivered through said lumen to pass outwardly through said holes, said balloon having an outer surface and carrying on said outer surface a tubular, substantially hydrophilic, microporous membrane covering said holes to break up streams of flowing medication, said balloon defining a central, generally cylindrical portion and tapered end portions having minimum diameter ends adhered to the catheter shaft, said tubular, microporous membrane being carried by the cylindrical portion of said balloon and spaced from the tapered end portions, the micropores of said membrane being essentially from 0.4 to 3 microns in diameter, the holes of said balloon being essentially from 5 to 100 microns in diameter.

11. The catheter of claim 10 in which said balloon defines a central portion of said generally cylindrical portion that is of less diameter than the ends of said cylindrical portion, whereby a generally cylindrical space is normally defined between central portions of said balloon and said microporous membrane.

12. The catheter of claim 11 in which the number of said micropores per square centimeter of said membrane is about 100,000 to 500,000,000.

13. The catheter of claim 12 in which the number of said holes in the balloon is essentially from 20 to 1,000.

14. The catheter of claim 13 in which said microporous membrane is coated with a hydrophilic agent.

15. The catheter of claim 10 in which the micropores of said membrane are smaller and more numerous than the holes of said balloon.

* * * * *